(12) United States Patent
Alsmadi (10) Patent No.: US 10,115,197 B1
(45) Date of Patent: Oct. 30, 2018

(54) APPARATUS AND METHOD FOR LESIONS SEGMENTATION

(71) Applicant: Imam Abdulrahman Bin Faisal University, Dammam (SA)

(72) Inventor: Mutasem K. Alsmadi, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 0 days.

(21) Appl. No.: 15/614,893

(22) Filed: Jun. 6, 2017

(51) Int. Cl.
*G06T 7/00* (2017.01)
*G06T 7/11* (2017.01)
*G06T 7/194* (2017.01)
*G06T 7/12* (2017.01)
*A61B 6/00* (2006.01)

(52) U.S. Cl.
CPC .............. *G06T 7/0012* (2013.01); *G06T 7/11* (2017.01); *G06T 7/194* (2017.01); *A61B 6/5217* (2013.01); *G06T 7/12* (2017.01); *G06T 2207/10116* (2013.01); *G06T 2207/20032* (2013.01); *G06T 2207/20116* (2013.01); *G06T 2207/30096* (2013.01)

(58) Field of Classification Search
CPC ........ A61B 6/5217; G06T 2207/10116; G06T 2207/20116; G06T 7/0012; G06T 7/12; G06T 7/149
See application file for complete search history.

(56) References Cited

U.S. PATENT DOCUMENTS

2013/0266197 A1* 10/2013 Nagenthiraja ........ G06T 7/0012
                                                          382/128
2016/0262686 A1    9/2016 Tsuji et al.

OTHER PUBLICATIONS

Yanhui Guo et al., "NCM: neutrosophic c-means clustering algorithm," pp. 1-42, Mar. 2015.

* cited by examiner

*Primary Examiner* — Kenny Cese
(74) *Attorney, Agent, or Firm* — Oblon, McClelland, Maier & Neustadt, L.L.P.

(57) ABSTRACT

An apparatus and method for performing image segmentation. The method includes the steps of filtering an X-ray image of a jaw of a patient to reduce noise. Each image pixel is clustered into one of a lesion region and a background region. Further, the method transforms each pixel included in the clustered image into a neutrosophic domain determined by computing a three-tuple including a first probability corresponding to the pixel being correctly clustered in the lesion region, a second probability corresponding to the pixel being incorrectly clustered, and a third probability corresponding to the pixel being indeterminate, and iteratively computes the first probability, the second probability, and the third probability based on a mean value of pixel intensity of a predetermined window and a homogeneity value. The image is segmented by assigning the indeterminate pixels the lesion region or the background region based on a degree of pixel indeterminacy.

18 Claims, 9 Drawing Sheets

APPARATUS AND METHOD FOR LESIONS SEGMENTATION

FIELD

The present disclosure relates to an apparatus and method of segmenting images to detect lesions. For instance, embodiments of the present disclosure can be applied to detect lesions in a jaw of a patient.

BACKGROUND

The background description provided herein is for the purpose of generally presenting the context of the disclosure. Work of the presently named inventor(s), to the extent the work is described in this background section, as well as aspects of the description that may not otherwise qualify as prior art at the time of filing, are neither expressly nor impliedly admitted as prior art against the present disclosure.

Radiography is one of the most helpful and common diagnostic tools available to dental practitioners. X-rays usage as a standard diagnostic procedure is well established in the profession. It is important to get as much as possible diagnostic information from X-ray images. A differential diagnosis could be performed using X-ray images. Conventional films are used commonly in radiologic examination to evaluate jaw cysts and odontogenic tumors. X-ray imaging is easy, convenient to use and reproducible method. The equipment is relatively cheap compared with other advanced imaging modalities. The images are easy to read once the observer is trained. They are also simple to store and retrieve. Diagnosis could be performed as soon as the image is taken.

White et al. introduced the Oral Radiographic Deferential Diagnosis (ORAD) program that is based on a questionnaire that was designed to evaluate the clinical and radiographic features of patients with intra-bony lesions using Bayes' theorem, in their work "Computer-aided differential diagnosis of oral radio-graphic lesions", Dentomaxillofacial Radiol 1989; 18(2):53-9, which is incorporated herein by reference in its entirety. The aim of ORAD program is to assist in lesions identification. Ninety-eight jaw lesions were described by many features such as their prevalence and distribution by race, sex, age, and the presence of pain, size, number, and location of lesions, association with teeth, jocularity, expansion, contents, borders and impact on adjacent teeth, and wherein a menu of sixteen questions is utilized to characterize a specific lesion.

A list of the lesions is introduced as output in order of their estimated probability. In addition, an estimate of the match extent between the lesion and the appearance of each lesion in the knowledge base is calculated. Preliminary tests indicate that ORAD is useful in assisting clinicians in formulating a differential diagnosis.

Radiologists usually analyze X-ray images by extracting features from the border of the lesion, internal structures, placement and resorption of the teeth. Many steps are required to evaluate radiopaque jaw lesion. The first and most important step is to categorize the lesion by its attenuation, and its location with respect to the tooth. These observations are essential for the evaluation of any type of jaw lesion. Then it will be easy to create a proper differential diagnosis. Perilesional halo, growth pattern, bone expansion, and margin as well as the type of lesion—whether it is sclerotic, has ground-glass attenuation, or is mixed lytic and sclerotic are all important features that narrow the differential diagnosis. To explore the "terra incognita" of radiopaque jaw lesions it is important to be aware of the associated clinical features and their demographic distribution, as well as the radiologic approach.

Radiologists are frequently consulted to evaluate a variety of jaw lesions or may incidentally encounter these lesions on routine patient's checkup. It is important to have a diagnostic approach pattern when faced with an unknown jaw lesion. Specific cardinal and additional radiographic criteria on plain film studies are important for differential diagnosis. The location with regard to the adjacent tooth structures within the jaw Cardinal and the density of the lesion are basic radiographic criteria. Other criteria in the jaw lesions evaluation are morphological characteristics, demarcation, periosteal, cortical involvement and soft tissue changes. Lesions could be categorized into two types, namely well-defined and poorly-defined. A well-defined lesion is a tumor representing a distinct radiolucency with a corticated margin. In a poorly defined lesion, the border is readily identified but is not corticated. A diffuse border is characterized by a margin that could not be distinguished and the transitional zone between the lesion and unaffected bone is wide and indistinct. The internal structures indicate the type of trabeculations.

Some jaw lesions have characteristic radiographic appearance such as ameloblastoma which usually appear as a multi-locular cyst like lesion of the jaw (honeycomb), while osteosarcoma appears usually as sunray radiopacity. On the other hand, myxoma is described as delicate filamentous structures that tend to be angular and form square, rectangular or triangular compartments. Some studies called this feature "tennis racquet" appearance. The internal structures are evaluated with reference to these trabeculations.

It is important to provide dentists with the tools that help them to assess their own accuracy at least for common diagnostic problems. A major step in improving dentist's diagnostic accuracy is to identify features on X-ray images correctly and accurately. Accordingly, there is a requirement to provide for an accurate method of performing jaw lesion segmentation.

SUMMARY

An aspect of the present disclosure provides for a method of performing image segmentation to detect lesions, the method comprising: receiving by circuitry an X-ray image of a region including the lesion; filtering the received image by a median filter to reduce speckle noise present in the received image, and forming a filtered image including a plurality of pixels; clustering each image pixel of the plurality of pixels in the filtered image into one of a lesion region and a background region, to form a clustered image; transforming each pixel included in the clustered image into a neutrosophic domain; determining by the circuitry, the neutrosophic domain of each pixel by computing a three-tuple including a first probability corresponding to the pixel being correctly clustered in the lesion region, a second probability corresponding to the pixel being incorrectly clustered in the lesion region, and a third probability corresponding to the pixel being an indeterminate pixel; iteratively computing by the circuitry, until a stop criterion is satisfied, the first probability, the second probability, and the third probability based on a mean value of pixel intensity of a predetermined window and a homogeneity value; and assigning the indeterminate pixel to one of the lesion region and the background region to segment the X-ray image upon the stopping criterion being satisfied, the assigning being performed based on a degree of pixel indeterminacy.

One aspect of the present disclosure is to provide an apparatus comprising: circuitry configured to: circuitry configured to receive an X-ray image of a region including the lesion, filter the received image by a median filter to reduce speckle noise present in the received image, and forming a filtered image including a plurality of pixels, cluster each image pixel of the plurality of pixels in the filtered image into one of a lesion region and a background region, to form a clustered image, transform each pixel included in the clustered image into a neutrosophic domain; determine the neutrosophic domain of each pixel by computing a three-tuple including a first probability corresponding to the pixel being correctly clustered in the lesion region, a second probability corresponding to the pixel being incorrectly clustered in the lesion region, and a third probability corresponding to the pixel being an indeterminate pixel, iteratively compute, until a stop criterion is satisfied, the first probability, the second probability, and the third probability based on a mean value of pixel intensity of a predetermined window and a homogeneity value, and assign the indeterminate pixel to one of the lesion region and the background region to segment the X-ray image upon the stopping criterion being satisfied, the assigning being performed based on a degree of pixel indeterminacy.

By one aspect of the present disclosure is provided a non-transitory computer readable medium including computer executable instructions that, when executed by a computer, causes the computer to execute a method of performing image segmentation to detect lesions, the method comprising: receiving an X-ray image of a region including the lesion; filtering the received image by a median filter to reduce speckle noise present in the received image, and forming a filtered image including a plurality of pixels; clustering each image pixel of the plurality of pixels in the filtered image into one of a lesion region and a background region, to form a clustered image; transforming each pixel included in the clustered image into a neutrosophic domain; determining the neutrosophic domain of each pixel by computing a three-tuple including a first probability corresponding to the pixel being correctly clustered in the lesion region, a second probability corresponding to the pixel being incorrectly clustered in the lesion region, and a third probability corresponding to the pixel being an indeterminate pixel; iteratively computing, until a stop criterion is satisfied, the first probability, the second probability, and the third probability based on a mean value of pixel intensity of a predetermined window and a homogeneity value; and assigning the indeterminate pixel to one of the lesion region and the background region to segment the X-ray image upon the stopping criterion being satisfied, the assigning being performed based on a degree of pixel indeterminacy.

The foregoing paragraphs have been provided by way of general introduction, and are not intended to limit the scope of the following claims. The described embodiments together, with further advantages, will be best understood by reference to the following detailed description taken in conjunction with the accompanying drawings.

BRIEF DESCRIPTION OF THE DRAWINGS

Various embodiments of the present disclosure that are provided as examples will be described in detail with reference to the following figures, wherein like numerals reference like elements, and wherein.

DETAILED DESCRIPTION

Exemplary embodiments are illustrated in the referenced figures of the drawings. It is intended that the embodiments and figures disclosed herein are to be considered illustrative rather than restrictive. No limitation on the scope of the technology and of the claims that follow is to be imputed to the examples shown in the drawings and discussed herein.

The embodiments are mainly described in terms of particular processes and systems provided in particular implementations. However, the processes and systems will operate effectively in other implementations. Phrases such as "an embodiment", "one embodiment" and "another embodiment" may refer to the same or different embodiments. The embodiments will be described with respect to methods and compositions having certain components. However, the methods and compositions may include more or less components than those shown, and variations in the arrangement and type of the components may be made without departing from the scope of the present disclosure.

The exemplary embodiments are described in the context of methods having certain steps. However, the methods and compositions operate effectively with additional steps and steps in different orders that are not inconsistent with the exemplary embodiments. Thus, the present disclosure is not intended to be limited to the embodiments shown, but is to be accorded the widest scope consistent with the principles and features described herein and as limited only by the appended claims.

Furthermore, where a range of values is provided, it is to be understood that each intervening value between an upper and lower limit of the range and any other stated or intervening value in that stated range is encompassed within the disclosure. Where the stated range includes upper and lower limits, ranges excluding either of those limits are also included. Unless expressly stated, the terms used herein are intended to have the plain and ordinary meaning as understood by those of ordinary skill in the art. The following definitions are intended to aid the reader in understanding the present disclosure, but are not intended to vary or otherwise limit the meaning of such terms unless specifically indicated.

The mandible and maxilla (jaw) like other bones suffer from hundreds of generalized and localized lesions and neoplasms. Some of these lesions or tumors arise from the dental formative tissues, and therefore, are called odontogenic, which can be divided according to its development stage or tissues from which the tumor arose. Lesions or neoplasms arising from non-dental formative tissues are called non-odontogenic.

Inflammatory cysts are considered as one of the most common odontogenic and non-odontogenic jaw lesions followed by dentigerous cyst. In a total of 7412 oral lesions, a study by Khosravi et al. in "Demographic distribution of odontogenic cysts in Isfahan (Iran) over a 23-year period (1988-2010)", Dent Res J 2013; 10(2):162-7, incorporated herein by reference in its entirety, found that radicular inflammatory cysts are the most common jaw lesions accounting for 35.12% of the total odontogenic cysts reported in the study.

Although osteosarcoma is a rare neoplasm, its early detection is very important to improve the prognosis as the survival of patients with osteosarcoma is usually less than 5 years. As described in Rajendran R. Shafer's textbook of oral pathology. 6th Ed, 2009, and the work by Bhadage C, et al. in "Osteosarcoma of the mandible mimicking an odontogenic abscess: a case report and review of the literature", Dent Update 2013; 40(3):216-21, each incorporated herein by reference in their entirety, the diagnosing jaw lesions and its early detection is one of the important challenges in oral health care.

By one embodiment of the present disclosure is provided a method of performing jaw lesion segmentation based on a neutrosophic approach. Neutrosophy is a branch that studies the origin, nature, and scope of neutralities, as well as their interactions with different ideational spectra. For instance, the work of Smarandache. F. in "A unifying field in logics: neutrosophic logic, Neutrosophy, neutrosophic set, neutrosophic probability. 3rd ed. p. 143; and the work of Guo Y et al. in "NCM: neutrosophic c-means clustering algorithm", Pattern Recognition 2015; 48(8):2710-24, each incorporated herein by reference in their entirety, describe neutrosophic logic. Neutrosophic logic is a branch that generalizes fuzzy logic, and deals with paradoxes, contradictions, antitheses, antinomies.

Figure 1:
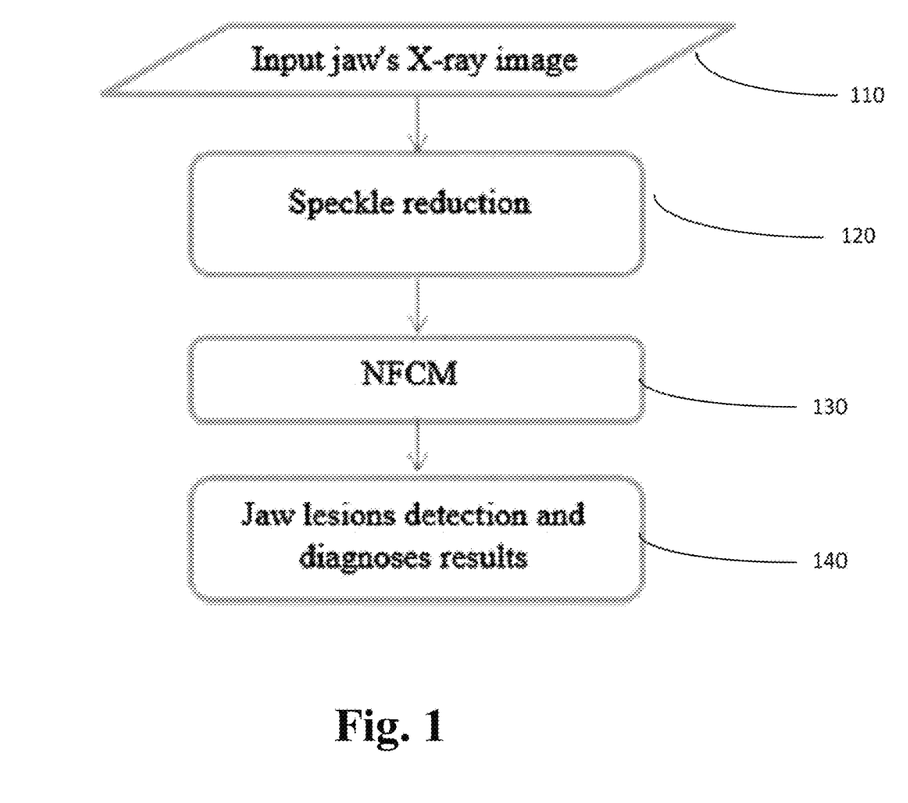
FIG. 1 illustrates an exemplary flowchart depicting the steps performed in a segmentation process.

According to one embodiment, a panoramic jaw's X-ray image segmentation approach includes four phases as shown in FIG. 1. The four phases (steps 110-140) may be carried out automatically, namely: speckle reduction, image enhancement, a clustering approach (NFCM) and lesion detection. The four phases are explained in detail below.

Determining the region of interest is not applicable to the jaw's images, due to the small lesion area compared to the constructions present in the panoramic jaw's X-ray image (fat, connective tissue, teeth and muscles). Accordingly, by one embodiment, speckle reduction is thus applied on the whole jaw's X-ray image instead of the region of interest, and median filter of size m=3*3 is applied to remove and reduce the speckle noise. For example, a filter as described by Anter A, et al, in Neutrosophic sets and fuzzy C-means clustering for improving CT liver image segmentation. In: Kömer P, Abraham A, Snás el V, editors, proceedings of the fifth international conference on innovations in bio-inspired computing and applications IBICA 2014, Springer International Publishing; 2014. p. 193-203, which is incorporated herein by reference in its entirety can be applied. Median filters provide excellent speckle reduction abilities for certain types of speckle noise compared with other filters such as linear smoothing filters of similar size.

By one embodiment, a new clustering approach (NFCM) that groups and clusters jaw's X-ray image pixels into background region and lesion region is described herein.

Fuzzy C-Means (FCM) is a strong clustering method which permits one data piece to belong to two or more clusters, as described by Alsmadi M in "A hybrid firefly algorithm with fuzzy-C mean algorithm for MRI brain segmentation", Am J Appl Sci 2014; 11 (9):1676-91 which is incorporated herein by reference in their entirety. The method relies on minimizing the objective function as follows:

$$J_m = \sum_{i=1}^{n} \sum_{j=1}^{c} u_{ij}^m \|x_i - c_j\|^2, 1 \leq m < \infty \qquad (1)$$

where m is any real number greater than 1 which represents the fuzziness exponent, $u_{ij}$ denote the membership of $x_i$ in cluster J, $x_i$ and $c_j$ denote the ith data point and cluster center of J, $\|\bullet\|$ is a norm representing the match between the data point and the cluster center. Iterative optimization was the method used to achieve fuzzy partitioning using the objective function and with updating the membership $u_{ij}$ and cluster center $c_j$ using the following equations:

$$u_{ij} = \frac{1}{\sum_{n=1}^{c} \left(\left\|\frac{x_i - c_j}{x_i - c_j}\right\|\right)^{\frac{1}{m-1}}} \qquad (2)$$

$$c_j = \frac{\sum_{i=1}^{N} u_{ij}^m \cdot x_i}{\sum_{i=1}^{N} u_{ij}^m} \qquad (3)$$

The Iterative optimization will stop when $$\max_{ij}\{|u_{ij}^{(k+1)} - u_{ij}^{(k)}|\} < \varepsilon \qquad (4)$$

Further, by one embodiment, concept of neutrosophy is applied in the segmentation of jaw images. The advantage of the neutrosophy is the high noise reduction without image boundary blurring. Thus, the result of segmentation is highly improved after the reduction in noise. The neutrosophy represents every pixel in the segmented image by three Neutrosophic constituents: f %, false, i % indeterminate, and t % true. The most beneficial component of neutrosophy is that indeterminacy is considered.

By one embodiment, the pixels of noise in the panoramic jaw images have a high degree of indeterminacy while the pixels of the lesion region have a low degree of indeterminacy. Accordingly, the two groups of pixels can be handled based on the degree of indeterminacy separately. Thus, noise is iteratively reduced and the lesion region is strengthened or untouched. In other words, an embodiment of the present disclosure explores a novel neutrosophy application by combining Fuzzy C-Means with the domain components of neutrosophy, thus achieving better treatment of the uncertainty data points. It must be appreciated that the clustering approach is an unsupervised learning approach which is dynamic and adaptive.

By one embodiment, the NFCM approach is applied to solve jaw's X-ray image segmentation problem, where the NFCM is used to determine the lesion from the background in the jaw's X-ray image. In what follows is described the Neutrosophic pixel and its Neutrosophic components in order to solve jaw's X-ray image segmentation problem as follows:

Neutrosophic set: Let U be the universe of the pixels, and L be a foreground set $L \subset U$. A pixel P is represented as p(T', I' and F'), belongs to A as following: it is t % true in the lesion pixel set, i % indeterminate, and f % false, where t varies in T', i varies in I', and f varies in F'. T', I' and F' are standard real subsets of with the range [0, 1+]. Thus, $0 \leq T'+I'+F' \leq 3$.

Neutrosophic image: The image domain of the pixel P(i, j) is transformed into Neutrosophic domain $P_{NS}(i, j)=\{T(i, j), I(i, j), F(i, j)\}$, here, T(i, j), I(i, j) and F(i, j) are the probabilities that belong to lesion region, indeterminate and background sets respectively, which are explained as follows:

$$T(i, j) = \frac{\overline{g(i, j)} - g_{min}}{g_{max} - g_{min}} \quad (5)$$

$$I(i, j) = 1 - \frac{Ho(i, j) - Ho_{min}}{Ho_{max} - Ho_{min}} \quad (6)$$

$$F(i, j) = 1 - T(i, j) \quad (7)$$

$$Ho(i, j) = abs(g(i, j) - \overline{g(i, j)}) \quad (8)$$

The local mean value is represented by $\overline{g(i,j)}$. The homogeneity value of T at (i, j) is represented by Ho(i, j), which is defined through the absolute value of variance between intensity g(i, j) And its local mean value $\overline{g(i,j)}$.

Further, in order to evaluate the distribution of different gray level in jaw's X-ray image, entropy of NS is applied. Thus, if the entropy is small, the intensities have diverse probabilities and the intensities distribution is non-uniform. If the entropy is the maximum, the different intensities will have similar probabilities and the intensity distribution is uniform.

Entropy of NS image: entropy of NS image is explained as the summation of the entropies of three subsets T, I and F, which is employed in this work to evaluate and measure the elements distribution in the NS domain. Thus, the following conditions hold true:

$$En_T = -\Sigma P_T(i) \ln P_T(i) \quad (9)$$

$$En_I = -\Sigma P_I(i) \ln P_I(i) \quad (10)$$

$$En_F = -\Sigma P_F(i) \ln P_F(i) \quad (11)$$

$$En_{NS} = En_T + En_I + En_F \quad (12)$$

where the entropy of subset T is $En_T$, the entropy of subset I is $En_I$ and the entropy of subset F is $En_F$. The element i probabilities in T, I and F are denoted as $P_T(i)$, $P_I(i)$, and $P_F(i)$ respectively. $En_F$ and $En_T$ are employed to measure the elements distribute in NS, and to evaluate the indeterminacy distribution, $En_I$ is utilized.

By one embodiment of the present disclosure, a λ-mean operation is implemented to measure the indeterminate degree. Specifically, the I(i, j) value is employed in order to measure the indeterminate degree of element $P_{ns}(i, j)$. The following equation was used to make subset I correlated with the other subsets (T, F), where the change in both subsets (T, F) affect the element distribution in I and the I entropy.

$$\overline{G}(i, j) = \frac{1}{w * w} \sum_{x=i-w/2}^{i+w/2} \sum_{y=j-w/2}^{j+w/2} G(x, y) \quad (13)$$

where w represented the size of window and $\overline{G}(i, j)$ was the value of intensity. Through the use of the aforesaid equation, an indeterminate pixel (with high indeterminacy) in the background will be progressively integrated into the background, while an indeterminate pixel (with low indeterminacy) inside a lesion will be progressively assimilated into the lesion region.

In what follows is described a clustering approach based on the hybridization between Neutrosophic sets with Fuzzy C-Mean clustering (NFCM), and the proposed hybridization approach includes of the following steps:

1. Initiate membership matrix $U^l=[u_{wz}]$; the value of l is 0, w represents the pixel index, z represents the cluster index and/represents the number of iteration.
2. l=l+1. Calculate $T^j$, $I^j$ and $F^j$ at each iteration for image $G^j$ using Est. (5), (6) and (7).
3. Transform $T^j$, $I^j$ and $F^j$ into vectors VT, VI and VF.
4. Then, calculate the center vector $L^j=[v_q]$ by $U^j$, VT, VI and VF.

$$C_v = \frac{\sum_{x=1}^{N} u_{wz}^m \cdot (1 - VI_x) \cdot VT_x \cdot VF_x}{\sum_{x=1}^{N} u_{wz}^m \cdot (1 - VI_x)} \quad (14)$$

where N is the total number of the image pixels, m represents the membership parameter.

5. Update membership matrix $U^{l+1}=[u_{wz}]$ using $$u_{wz} = \frac{1}{\sum_{d=1}^{C} \left(\left\|\frac{VT_x - C_y}{VT_x - C_d}\right\|\right)^{\frac{2}{m-1}}} \quad (15)$$

where C is the cluster number.

6. λ=mean operation for $P_{NS}$, $P'_{NS}$ is used to update $G^j$ image which is defined as follows:

$$P'_{NS}(\lambda) = P(T'(\lambda), I'(\lambda), F'(\lambda)) \quad (16)$$

$$T'_\lambda = \begin{cases} T & \text{if } I < \lambda \\ T' & \text{if } I \geq \lambda \end{cases} \quad (17)$$

-continued $$T'_\lambda(i, j) = \frac{1}{w*w} \sum_{x=i-w/2}^{i+w/2} \sum_{y=j-w/2}^{j+w/2} T(x, y) \quad (18)$$

$$F'_\lambda = \begin{cases} F & \text{if } I < \lambda \\ F' & \text{if } I \geq \lambda \end{cases} \quad (19)$$

$$F'_\lambda(i, j) = \frac{1}{w*w} \sum_{x=i-w/2}^{i+w/2} \sum_{y=j-w/2}^{j+w/2} T(x, y) \quad (20)$$

$$I'_\lambda(i, j) = 1 - \frac{Ho'(i, j) - Ho'_{min}}{Ho'_{max} - Ho'_{min}} \quad (21)$$

where w is the window size, (i, j) is the pixel at the window center and λ is the threshold of indeterminacy.

7. If $\|U^{l+1} - U^l\| < \varepsilon$, stop; if not return to step 2.

According to one embodiment, C=2 since the image has two clusters; λ=0.1, m=2 and w=5 where these values can be determined experimentally based on the dataset.

By one embodiment, in order to measure the efficiency of the above described NFCM segmentation process, the NFCM process is compared with other segmentation methods, namely; the Hybrid Firefly Algorithm with FCM (FAFCM), and the Artificial Bee Colony with FCM (ABCFCM). These segmentation methods have been employed in order to make a fair comparison with NFCM using the same common criteria and dataset used (real dataset of jaw's panoramic X-ray images), and FAFCM and ABCFCM have been applied in a similar manner. Since there is no public benchmark and no globally accepted assessment criteria yet, three comprehensive metrics (Area error metrics, specificity and sensitivity metrics) have been used in this work to compare results from different aspects.

By one embodiment, the experiments are performed based on real dataset of jaw's panoramic X-ray images. These dataset includes 95 jaw's panoramic X-ray images, 60 images have malignant cases, and 35 images have benign cases as confirmed by pathology. The dataset was collected from the radiology archives of the College of Dentistry and main referral hospitals in the Eastern Province such as King Fahd Hospital of the University and Dammam Central Hospital. The histopathological slides of each lesion have been reviewed by Oral Pathologist to confirm the diagnosis of the radiographic lesion.

In one such experiment, 10 panoramic X-ray images have been analyzed for each jaw tumor based on the WHO classification of tumors and jaw lesions according to oral pathology classification of jaw lesions. The boundaries of every lesion in jaw's panoramic X-ray image are delineated by an experienced Oral Pathologist and the manual delineation served as a standard reference.

By one embodiment, in order to measure how much the Jaw lesion region in the panoramic X-ray image is covered correctly by the generated lesion region, and how much portion is covered incorrectly, an area error metrics is used. Specifically, an area ratio of the false positive (FP), true positive (TP) and false negative (FN) is calculated as following:

$$TP = \frac{|A_m \cap A_a|}{|A_m|} \quad (22)$$

$$FP = \frac{|A_m \cup A_a - A_m|}{|A_m|} \quad (23)$$

$$FN = 1 - TP = \frac{|A_m \cup A_a - A_a|}{|A_m|} \quad (24)$$

In the above equations, the manually determined lesion region (pixel set) by Oral Pathologist is represented as $A_m$, and the automatically produced lesion region (pixel set) by the proposed approach is represented as $A_a$. Further, by one embodiment, a similarity Index (SI) is used to measure the closeness of the automatically produced lesion region to the lesion region determined by the Oral Pathologist. The following equation is used to calculate the SI.

$$SI = \frac{|A_m \cap A_a|}{|A_m \cup A_a|} \quad (25)$$

Moreover, by one embodiment of the present disclosure, specificity metric is used to measure the ability and effectiveness of an algorithm in segmenting or classifying the tissues correctly. The effectiveness of an algorithm in isolating the non-lesion region is represented as specificity. The proposed NFCM segments the non-lesion region of the law's efficiently and the validation results are clearly illustrated in Table 2 (shown below).

Furthermore, sensitivity value (SV) is used according to one embodiment, to represent the total number of images that have been correctly segmented and classified. Specifically, SV refers to the correctly lesion region identified. The following equation was used to calculate the SV.

$$SV = \frac{TP}{TP + FN} \quad (26)$$

Figure 2A:
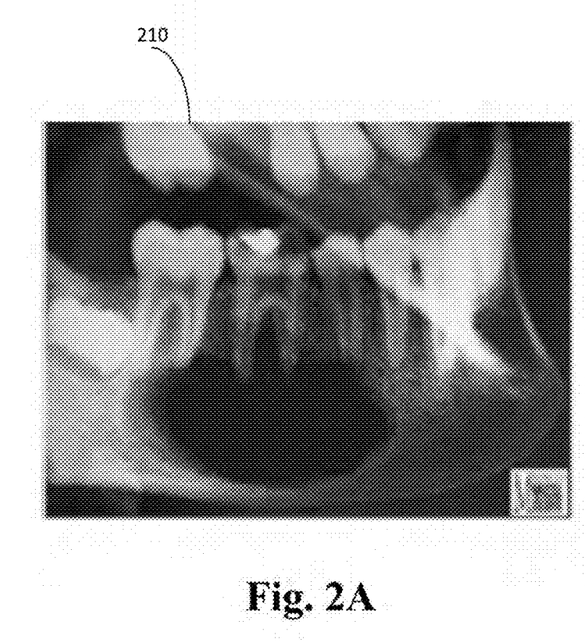
FIG. 2A illustrates by one embodiment, an original abnormal real jaw's panoramic X-ray images (periapical-lateral and residual cyst)
Figure 2B:
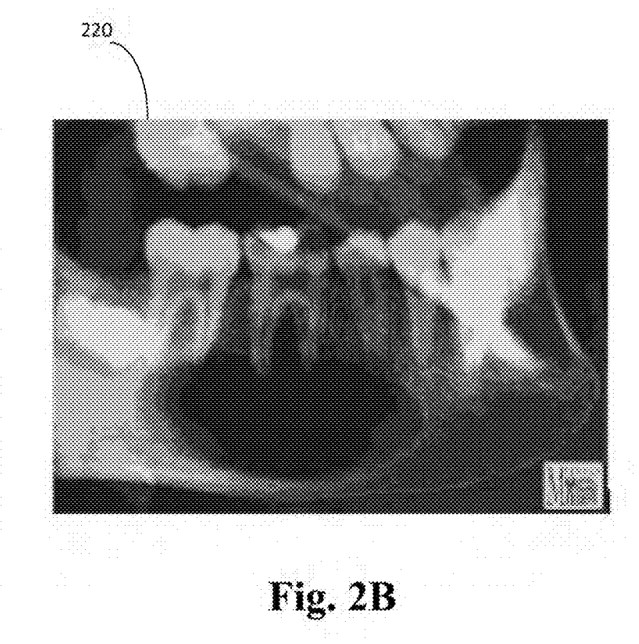
FIG. 2B illustrates according to an embodiment, illustrates segmented results acquired by Fuzzy-C-means (FCM)
Figure 2C:
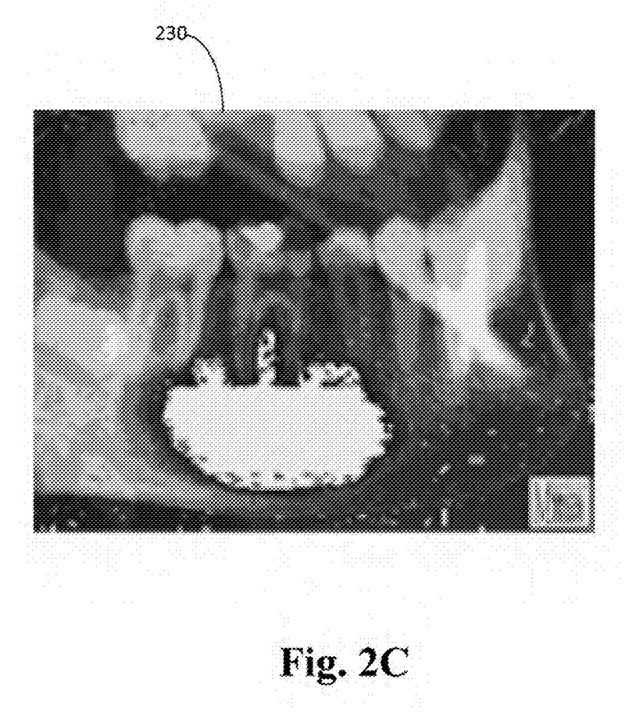
FIG. 2C illustrates according to an embodiment, segmented result acquired by Neutrosophic-Fuzzy-C-means (NFCM)
Figure 2D:
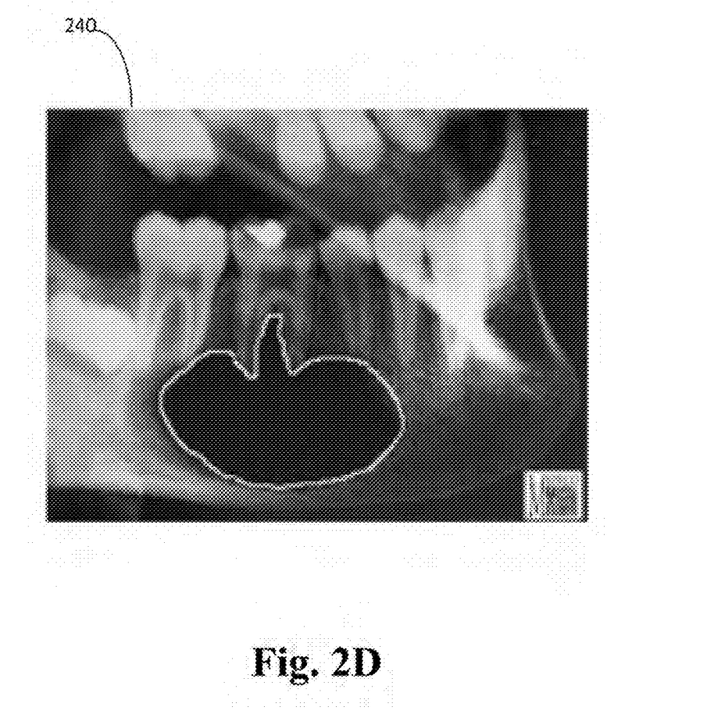
FIG. 2D illustrates according to an embodiment, manual delineation by Oral Pathologist.

By one embodiment of the present disclosure, the NFCM approach of segmentation as described herein is compared with the FCM technique using the same dataset, the same speckle reduction step is carried out exactly for both NFCM and FCM. FIGS. 2A-2D and 3A-3D illustrate the clustered abnormal real jaw's panoramic X-ray images (Periapical-lateral and residual cyst) using the FCM and NFCM methods, respectively. FIG. 2A illustrates the original abnormal real jaw's panoramic X-ray images (periapical-lateral and residual cyst) 210; FIG. 2B illustrates segmented results acquired by FCM, 220; FIG. 2C illustrates segmented result 230 acquired by the NFCM; and FIG. 2D illustrates manual delineation by Oral Pathologist 240.

Figure 3A:
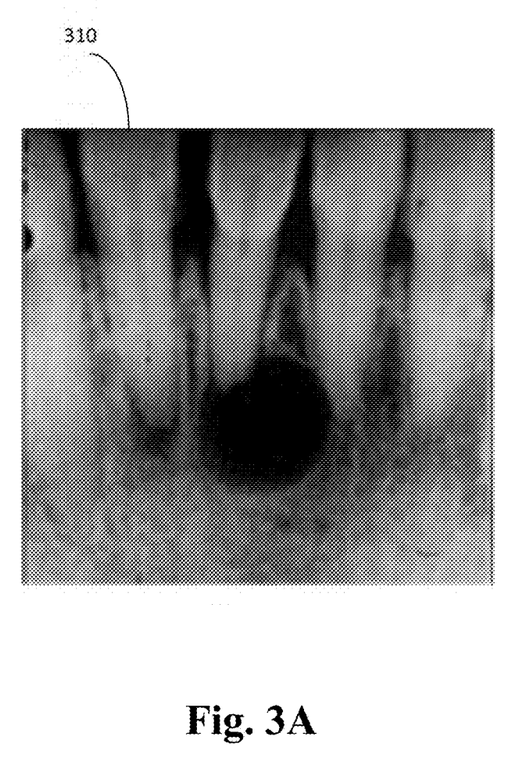
FIG. 3A illustrates by one embodiment, an original abnormal real jaw's panoramic X-ray images (periapical-lateral and residual cyst.
Figure 3B:
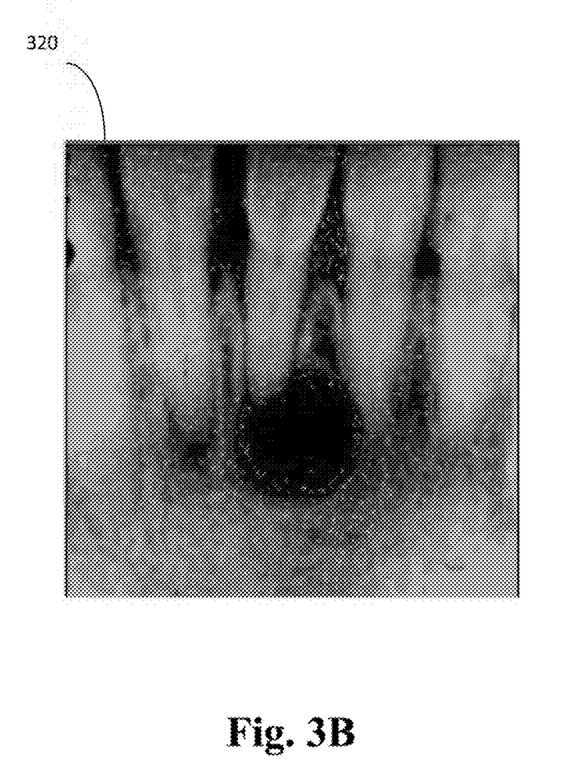
FIG. 3B illustrates by one embodiment segmented results acquired by FCM.
Figure 3C:
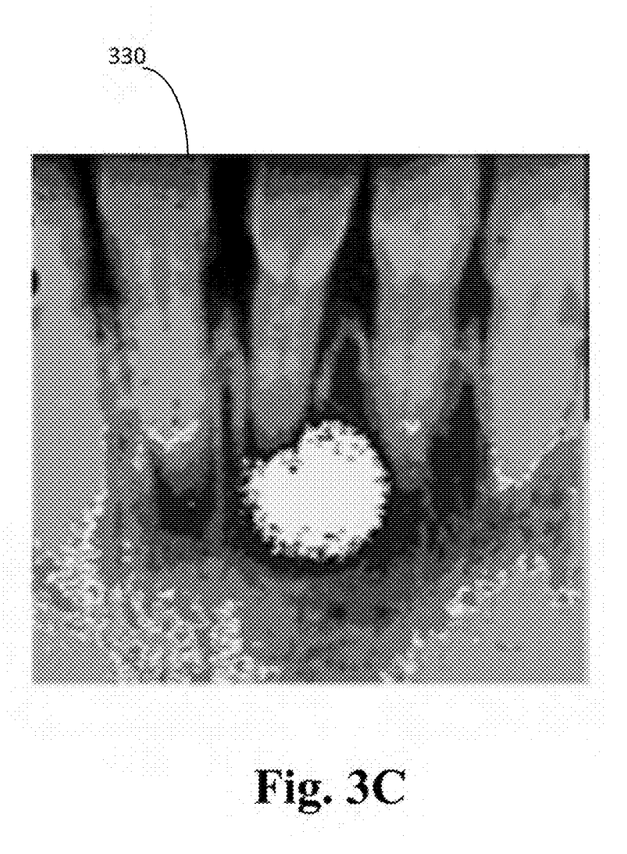
FIG. 3C illustrates by one embodiment a segmented result acquired by the NFCM.
Figure 3D:
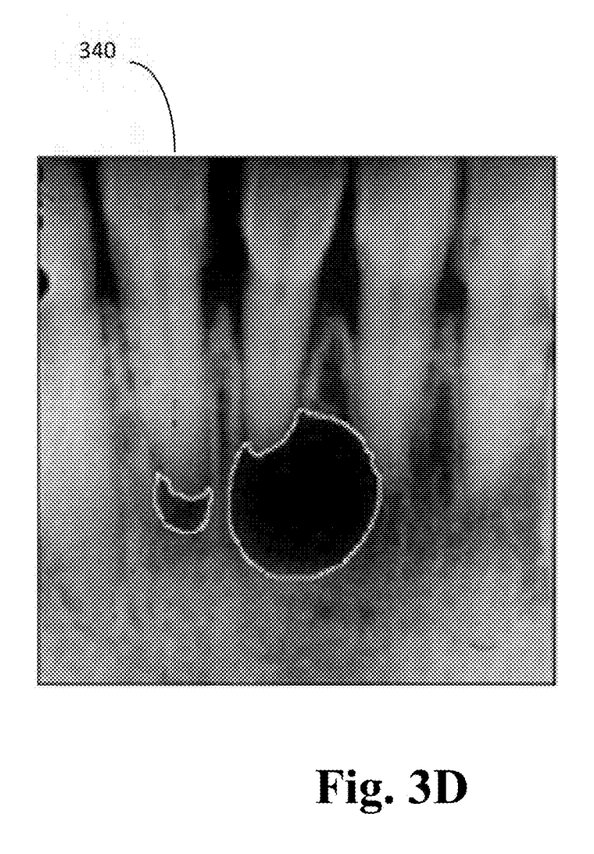
FIG. 3D illustrates by one embodiment manual delineation by Oral Pathologist.

In a similar manner, FIG. 3A illustrates the original abnormal real jaw's panoramic X-ray images (periapical-lateral and residual cyst) 310; FIG. 3B illustrates segmented results acquired by FCM, 320; FIG. 3C illustrates a segmented result acquired by the NFCM, 330; and FIG. 3D illustrates manual delineation by Oral Pathologist 340.

The resulting images, after applying the FCM and NFCM show the success of the NFCM in determining the lesion region automatically compared with FCM. FIGS. 2C and 3 C depict the existence of lesion in the lower jaw using the proposed NFCM, which was identical to the manual delineation by Oral Pathologist. The proposed NFCM is able to automatically determine the lesion region and the tumor cells number in the lesion region. The superiority of NFCM over FCM is that NFCM deals effectively and accurately with indeterminate regions. NFCM integrates the indeterminate pixels (with high indeterminacy) of jaw's panoramic X-ray images into background, while an indeterminate pixel (with low indeterminacy) inside a lesion is progressively assimilated into the lesion region.

In contrast, FCM misrecognizes the indeterminate pixels into lesion regions, since FCM uses only the distance to compute the cluster centers, regardless of the indeterminate degree. Moreover, NFCM can analyze the complex jaw's background and further detect the lesion region in the jaw's image.

As shown in Table 1, all the evaluation metrics using the entire database indicate that the proposed NFCM outperformed the FCM by obtaining much better averaging performance. Moreover, for each metric a P-value is measured. Statistically, when P-value 0.01, the observed difference is "highly significant", and if the P-value 0.05, the observed difference is "significant". The result of evaluation of the FCM and NFCM shows that the P-value for all evaluation metrics is less than 0.005 which means by the statistical criteria that the observed difference is "highly significant". The higher value of TP (enhanced from 83% to 90%) shows that NFCM covers more lesion region compared with FCM. The lower value of FP (decreased from 9.1% to 6.1%) shows that NFCM successfully determined the non-lesion regions compared with FCM.

TABLE 1

The obtained results from the FCM and the proposed NFCM.
Average of the area error metrics

| Approaches | FP (%) | TP (%) | FN | TN |
|---|---|---|---|---|
| FCM | 9.1 ± 8.5 | 83 ± 5.5 | 17 ± 5.5 | 90.9 ± 8.5 |
| Proposed NFCM | 6.1 ± 5.3 | 90 ± 2.5 | 10 ± 2.5 | 93.9 ± 5.3 |
| P-value | <0.005 | <0.005 | <0.005 | <0.005 |

By one embodiment of the present disclosure, in order to measure the efficiency of the proposed NFCM, the NFCM technique is compared with two segmentation methods (FAFCM and ABCFCM), and these segmentation methods have been employed in order to make a fair comparison with NFCM using the same common criteria and dataset. The parameters settings of the firefly algorithm are as follows: number of fireflies (n=110), max iteration=1000, $\beta$=1 and $\gamma$=1, and the parameters settings of the Artificial Bee Colony Algorithm are as follows: cycles number equals 2500 and colony size equals 50 bees.

Figure 4A:
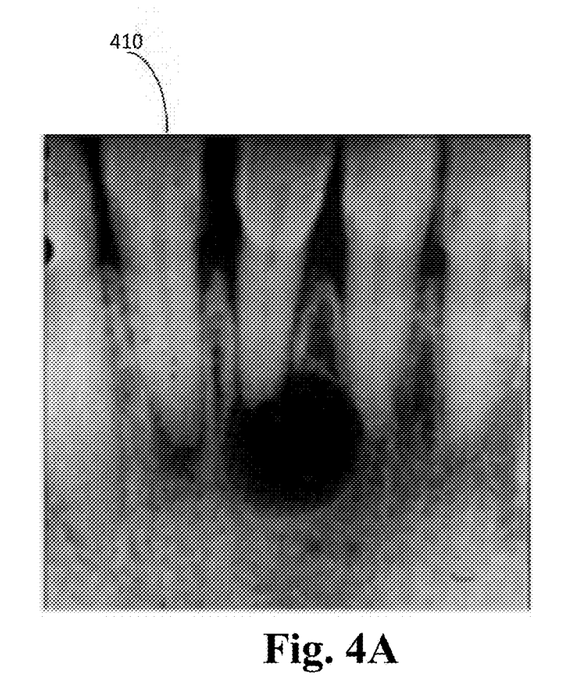
FIG. 4A illustrates an exemplary original abnormal real jaw's panoramic X-ray images (periapical-lateral and residual cyst)
Figure 4B:
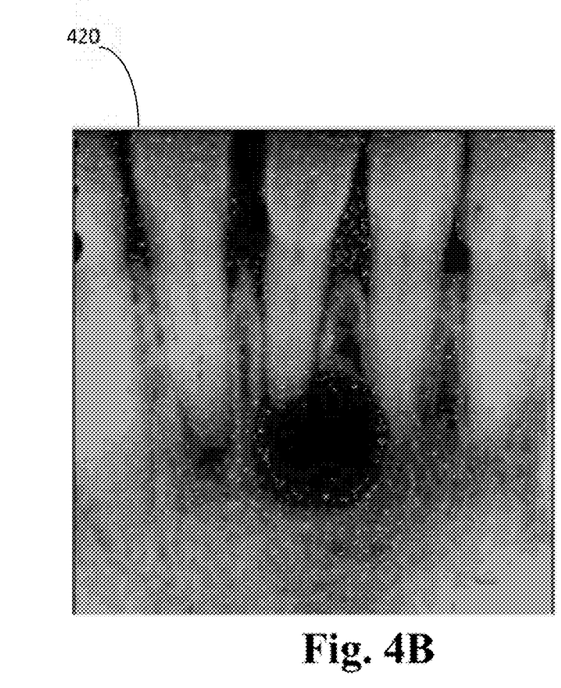
FIG. 4B illustrates an exemplary segmented result acquired by FCM.
Figure 4C:
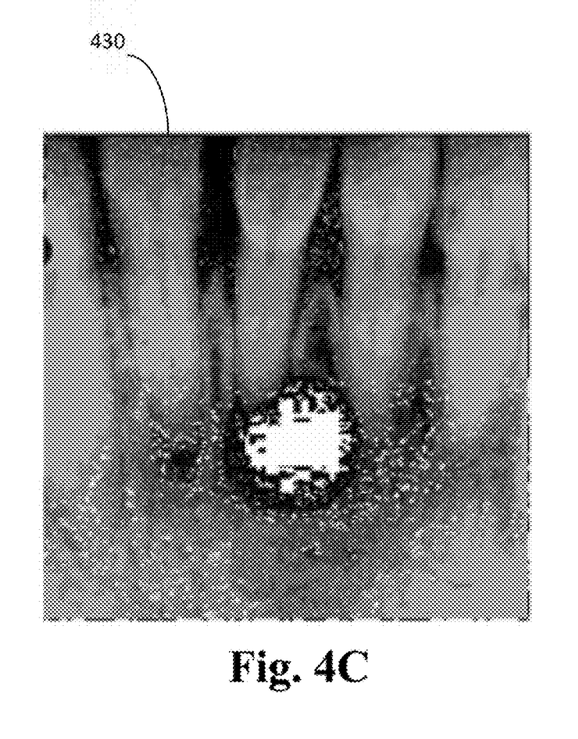
FIG. 4C illustrates an exemplary segmented result acquired by the ABCFCM method.
Figure 4D:
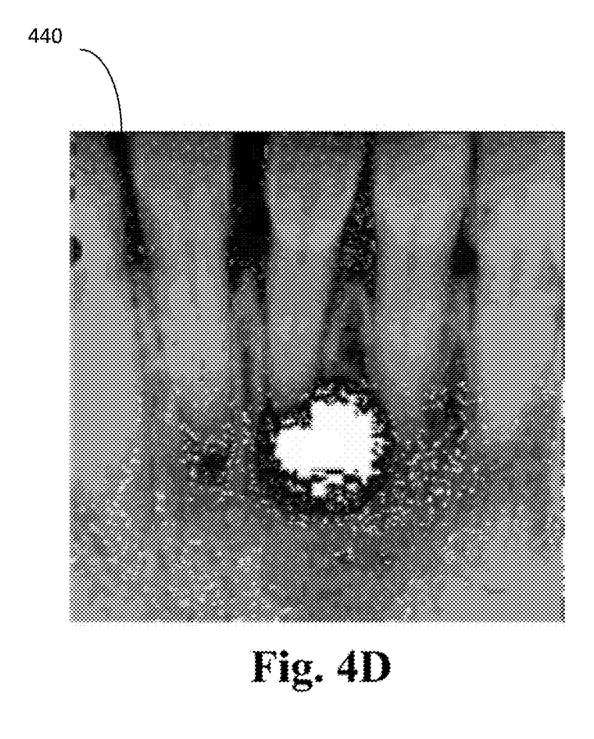
FIG. 4D illustrates by one embodiment, segmented result acquired by the FAFCM method.
Figure 5A:
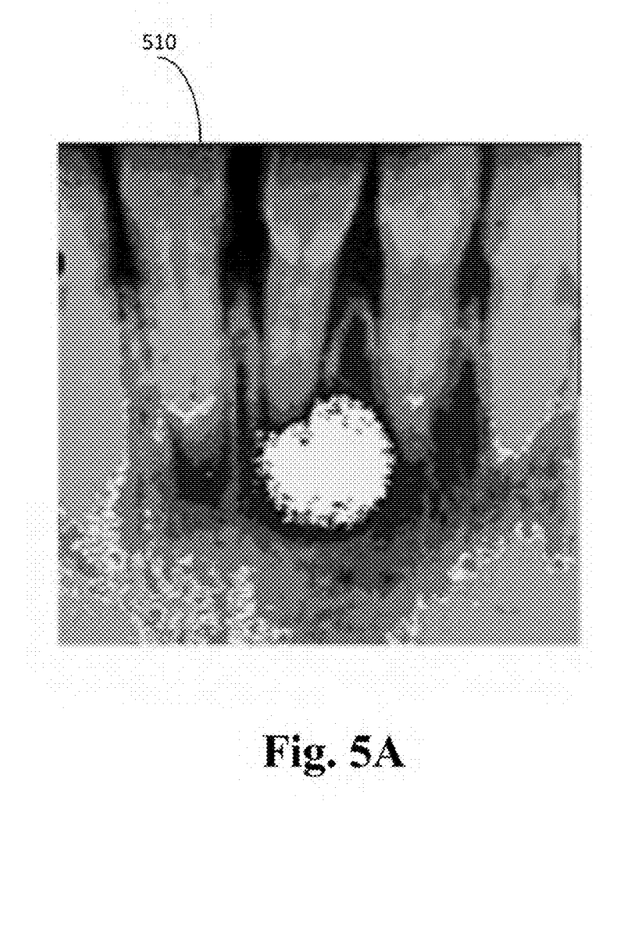
FIG. 5A illustrates exemplary segmented result acquired by the NFCM.
Figure 5B:
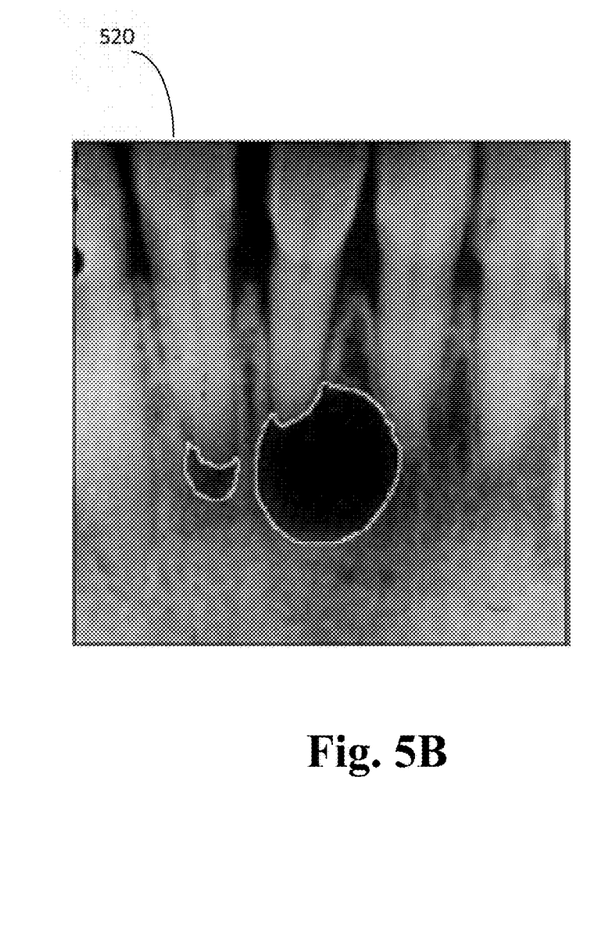
FIG. 5B illustrates exemplary manual delineation by Oral Pathologist.

In FIGS. 4A-4D and 5A-5B, the segmentation results of the segmentation methods (ABCFCM and FAFCM) are provided. FIG. 4A depicts the original abnormal real jaw's panoramic X-ray images (Periapical-lateral and residual cyst) 410, FIG. 4B depicts the segmented result acquired by FCM, 420, FIG. 4C illustrates the segmented result acquired by the ABCFCM, 430, and FIG. 4D illustrates segmented result acquired by the FAFCM, 440. Further, FIG. 5A depicts the segmented result acquired by the NFCM 510, and FIG. 5B depicts the manual delineation by Oral Pathologist, 520, respectively. The lesion regions detected by the proposed NFCM are more accurate and much closer to the Oral Pathologist manual delineation than those of ABCFCM and FAFCM.

Table 2 depicts the effectiveness of the NFCM method of the present disclosure in terms of SI, specificity and sensitivity compared with other methods. For a good and accurate segmentation method, specificity and sensitivity values should be close to 1. NFCM algorithm dominates the FCM, ABCFCM and FAFCM in terms of specificity and sensitivity, as shown in Table 3. The NFCM method outperforms the other FCM, ABCFCM and FAFCM algorithms as it has SI, specificity and sensitivity values of 0.9471, 0.9412 and 0.9592 respectively. Specificity and sensitivity values are calculated based on the comparison made between the manually determined lesion regions (pixel set) by the Oral Pathologist and the automatically produced lesion region (pixel set) by the proposed algorithms.

TABLE 2

Comparison results for Similarity Index (SI),
sensitivity and specificity values.

| Algorithms | Similarity Index (SI) | Specificity | Sensitivity |
|---|---|---|---|
| FCM | 0.8000 | 0.7723 | 0.8345 |
| ABCFCM | 0.9022 | 0.9122 | 0.925 |
| FAFCM | 0.9313 | 0.9213 | 0.943 |
| NFCM | 0.9471 | 0.9412 | 0.9592 |

As shown in the FIGS. 4A-4D, the NFCM method achieves a better performance as that compared with the FCM, FAFCM, and ABCFCM method respectively. Specifically, the NFCM method detects the lesion region more accurately that its counterparts. On the other hand, the computation time for the NFCM may be higher as compared with the others as shown in Table 3 below.

TABLE 3

The performance of the proposed NFCM and the results of
other segmentation algorithms (time calculation).

| | Normal | Abnormal image | | |
|---|---|---|---|---|
| Method | image Adults image | Periapical lateral and residual cyst-1 | Periapical lateral and residual cyst-2 | Primordial and OKC |
| FCM | 0.41 | 0.47 | 0.48 | 0.51 |
| FAFCM | 0.41 | 0.54 | 0.56 | 0.57 |
| ABCFCM | 0.42 | 0.52 | 0.57 | 0.51 |
| NFCM | 0.46 | 0.57 | 0.59 | 1.02 |

Table 4 depicted below illustrates the number of tumor regions detected (which are real lesions) and number of air gap regions (which are not real lesions) in the upper or lower jaw's panoramic X-ray image using the NFCM technique of the present disclosure.

TABLE 4

Number of regions detected (which are real lesions)
and number of air gap regions (which are not real lesions) in
the upper or lower jaw using the proposed NFCM.

| | Real lesion region | | Air gap region | |
|---|---|---|---|---|
| Image # | Upper jaw | Lower jaw | Upper jaw | Lower jaw |
| 1 | 0 | 2 | 0 | 1 |
| 2 | 0 | 2 | 0 | 0 |
| 3 | 1 | 1 | 0 | 0 |
| 4 | 1 | 0 | 0 | 1 |
| 5 | 1 | 1 | 0 | 0 |
| 6 | 0 | 2 | 0 | 0 |
| 7 | 0 | 1 | 0 | 1 |
| 8 | 0 | 1 | 0 | 0 |
| 9 | 0 | 1 | 1 | 0 |
| 10 | 0 | 1 | 0 | 0 |

Moreover, the results obtained using the NFCM approach as described above is compared to other methods which use a segmentation system for cyst or tumor cases from dental panoramic images using only 24 panoramic images consisting of various cyst lesions, compared to dataset consisting of 95 jaw's panoramic X-ray images including 10 types of tumors. The other methods introduced a system for the segmentation and classification of abnormal and normal oral cancer images. In the other methods, the tumor region boundaries have been determined using two segmentation methods, using active contour models and Marker-Controlled Watershed Segmentation to determine the region of interest (tumor region). These algorithms (i.e., other methods) suffer from many drawbacks such as parameters settings, problems in algorithm initialization, lack of strength to image noise, which highly affect the final results if inappropriate tumor region is selected.

However, the NFCM algorithm described herein determines and segments the tumor region by indeterminacy degree, which is more accurate and robust to image noise. In other words, from the comparisons between NFCM and other segmentation techniques using clustering methods, NFCM has improved the segmentation and detection efficiency of the tumor regions in the real jaw images. One of the reasons behind this improvement is that indeterminacy degree is taken into consideration. As such, noise is iteratively reduced and the lesion region is strengthened or untouched, since real datasets have a lot of ambiguous data such as noise.

The above described embodiments present an automatic segmentation approach for panoramic X-ray images. The method includes speckle noise reduction and NFCM clustering. NFCM can be useful in pattern classification, data mining, machine learning and other related areas. NFCM can be used to segment and determine the lesion region of jaw in panoramic X-ray images which may help in diagnosing jaw lesions. NFCM can be helpful to all dentists in diagnosing jaw lesions. NFCM has several advantages which can be summarized as follows: it can be used to segment and find lesion region accurately even in the low-contrast and complicated jaw panoramic X-ray images, it is completely automatic, the proposed NFCM technique when compared with the ABCFCM and FAFCM produces the most identical lesion region to the manual delineation by the Oral Pathologist, greatly reduced noise without blurring the boundary of the image which significantly improved the segmentation results and shows better performance (FP rate is 6.1%, TP rate is 90%, specificity rate is 0.9412, sensitivity rate is 0.9592 and similarity rate is 0.9471), it has detected the lesion region more accurately and the computation time for the NFCM is higher if compared with other methods.

Additionally, it must be appreciated that the above described embodiments are in no manner restricted to utilize only X-ray images. Rather, the techniques of the above described embodiments can utilize one or more of a computed tomography (CT) image, a magnetic resonance image (MRI), positron emission tomography (PET) image, PET-CT, ultrasound, photography, and video images. Moreover, the techniques of the above embodiments may be used to detect lesions in bones (other than the jaw of the patient), as well lesions in an organ/tissue of the patient.

In some medical images, objects such as lesions or even organs may not always have fully closed contours with clear boundaries, due to limitations incurred in the acquisition techniques and/or devices, for example having low resolution and/or low dynamic range. In such cases, there is a high possibility of the tissues and organs being occluded.

Accordingly, the techniques of the above embodiments can be applied for detection of lesions in cases such as detection of lesions in breast ultrasound images, detection of lesions in the eye tissues of a patient, detection of lesions in more complex tubular structures such as anterior visual pathway, and the like. Further, in the case of detecting jaw lesions as described above, the above embodiments may be implemented by circuitry (included in a processing device, and described later with reference to FIG. 6). The processing device may be used by the endodontist in performing a complex procedure (e.g., a root-canal operation). For instance, the techniques of the present disclosure may be implemented to detect tissue, nerves and bones in an area surrounding the tooth on which the operation is to be performed. Accordingly, lesions (if any) disposed near the tooth in question can be detected and analyzed in a seamless manner by the techniques described herein.

By one embodiment, each of the functions of the described embodiments may be implemented by one or more processing circuits. A processing circuit includes a programmed processor (for example, processor 603 in FIG. 6), as a processor includes circuitry. A processing circuit also includes devices such as an application-specific integrated circuit (ASIC) and circuit components that are arranged to perform the recited functions.

Figure 6:
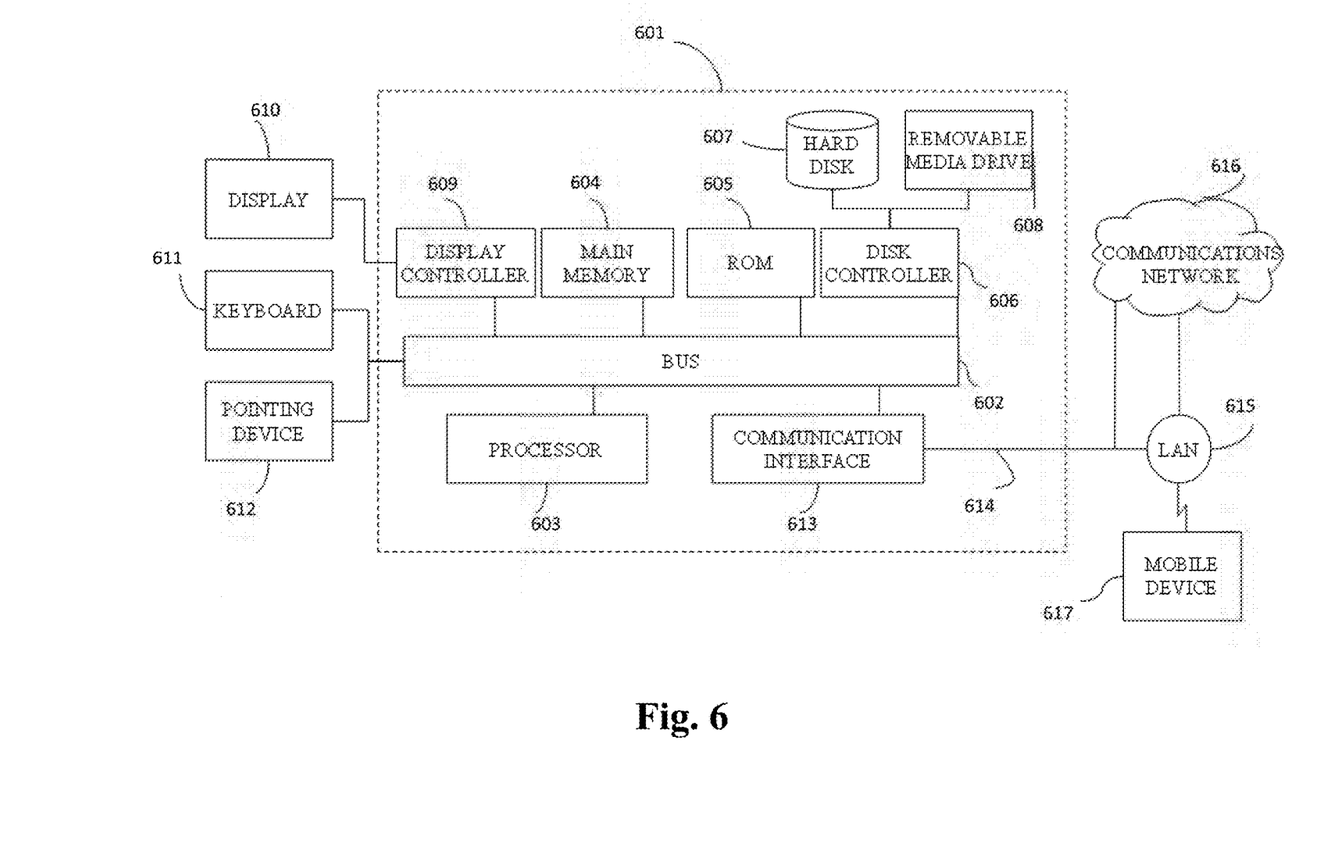
FIG. 6 illustrates a block diagram of a computing device according to one embodiment.

The various features discussed above may be implemented by a computer system (or programmable logic). FIG. 6 illustrates such a computer system 601. In one embodiment, the computer system 601 is a particular, special-purpose machine when the processor 603 is programmed to perform navigational processes of the vehicle, computing compensation path, and other functions described above.

The computer system 601 includes a disk controller 606 coupled to the bus 602 to control one or more storage devices for storing information and instructions, such as a magnetic hard disk 607, and a removable media drive 608 (e.g., floppy disk drive, read-only compact disc drive, read/write compact disc drive, compact disc jukebox, tape drive, and removable magneto-optical drive). The storage devices may be added to the computer system 601 using an appropriate device interface (e.g., small computer system interface (SCSI), integrated device electronics (IDE), enhanced-IDE (E-IDE), direct memory access (DMA), or ultra-DMA).

The computer system 601 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The computer system 601 may also include a display controller 609 coupled to the bus 602 to control a display 610, for displaying information to a computer user. The computer system includes input devices, such as a keyboard 611 and a pointing device 612, for interacting with a computer user and providing information to the processor 603. The pointing device 612, for example, may be a mouse, a trackball, a finger for a touch screen sensor, or a pointing stick for communicating direction information and command selections to the processor 603 and for controlling cursor movement on the display 610.

The processor 603 executes one or more sequences of one or more instructions contained in a memory, such as the main memory 604. Such instructions may be read into the main memory 604 from another computer readable medium, such as a hard disk 607 or a removable media drive 608. One or more processors in a multi-processing arrangement may also be employed to execute the sequences of instructions contained in main memory 604. In alternative embodiments, hard-wired circuitry may be used in place of or in combination with software instructions. Thus, embodiments are not limited to any specific combination of hardware circuitry and software.

As stated above, the computer system 601 includes at least one computer readable medium or memory for holding instructions programmed according to any of the teachings of the present disclosure and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes. Stored on any one or on a combination of computer readable media, the present disclosure includes software for controlling the computer system 601, for driving a device or devices for implementing the features of the present disclosure, and for enabling the computer system 601 to interact with a human user. Such software may include, but is not limited to, device drivers, operating systems, and applications software. Such computer readable media further includes the computer program product of the present disclosure for performing all or a portion (if processing is distributed) of the processing performed in implementing any portion of the present disclosure.

The computer code devices of the present embodiments may be any interpretable or executable code mechanism, including but not limited to scripts, interpretable programs, dynamic link libraries (DLLs), Java classes, and complete executable programs. Moreover, parts of the processing of the present embodiments may be distributed for better performance, reliability, and/or cost.

The term "computer readable medium" as used herein refers to any non-transitory medium that participates in providing instructions to the processor 603 for execution. A computer readable medium may take many forms, including but not limited to, non-volatile media or volatile media. Non-volatile media includes, for example, optical, magnetic disks, and magneto-optical disks, such as the hard disk 607 or the removable media drive 608. Volatile media includes dynamic memory, such as the main memory 604. Transmission media, on the contrary, includes coaxial cables, copper wire and fiber optics, including the wires that make up the bus 602. Transmission media also may also take the form of acoustic or light waves, such as those generated during radio wave and infrared data communications.

Various forms of computer readable media may be involved in carrying out one or more sequences of one or more instructions to processor 603 for execution. For example, the instructions may initially be carried on a magnetic disk of a remote computer. The remote computer can load the instructions for implementing all or a portion of the present disclosure remotely into a dynamic memory and send the instructions over a telephone line using a modem. A modem local to the computer system 601 may receive the data on the telephone line and place the data on the bus 602. The bus 602 carries the data to the main memory 604, from which the processor 603 retrieves and executes the instructions. The instructions received by the main memory 604 may optionally be stored on storage device 607 or 608 either before or after execution by processor 603.

The computer system 601 also includes a communication interface 613 coupled to the bus 602. The communication interface 613 provides a two-way data communication coupling to a network link 614 that is connected to, for example, a local area network (LAN) 615, or to another communications network 610 such as the Internet. For example, the communication interface 613 may be a network interface card to attach to any packet switched LAN. As another example, the communication interface 613 may be an integrated services digital network (ISDN) card. Wireless links may also be implemented. In any such implementation, the communication interface 613 sends and receives electrical, electromagnetic or optical signals that carry digital data streams representing various types of information.

The network link 614 typically provides data communication through one or more networks to other data devices. For example, the network link 614 may provide a connection to another computer through a local network 615 (e.g., a LAN) or through equipment operated by a service provider, which provides communication services through a communications network 610. The local network 614 and the communications network 610 use, for example, electrical, electromagnetic, or optical signals that carry digital data streams, and the associated physical layer (e.g., CAT 5 cable, coaxial cable, optical fiber, etc.). The signals through the various networks and the signals on the network link 614 and through the communication interface 613, which carry the digital data to and from the computer system 601 may be implemented in baseband signals, or carrier wave based signals.

The baseband signals convey the digital data as unmodulated electrical pulses that are descriptive of a stream of digital data bits, where the term "bits" is to be construed broadly to mean symbol, where each symbol conveys at least one or more information bits. The digital data may also be used to modulate a carrier wave, such as with amplitude, phase and/or frequency shift keyed signals that are propagated over a conductive media, or transmitted as electromagnetic waves through a propagation medium. Thus, the digital data may be sent as unmodulated baseband data through a "wired" communication channel and/or sent within a predetermined frequency band, different than baseband, by modulating a carrier wave. The computer system 601 can transmit and receive data, including program code, through the network(s) 615 and 610, the network link 614 and the communication interface 613. Moreover, the network link 614 may provide a connection through a LAN 615 to a mobile device 617 such as a personal digital assistant (PDA) laptop computer, or cellular telephone.

While aspects of the present disclosure have been described in conjunction with the specific embodiments thereof that are proposed as examples, alternatives, modifications, and variations to the examples may be made. It should be noted that, as used in the specification and the appended claims, the singular forms "a," "an," and "the" include plural referents unless the context clearly dictates otherwise.

Furthermore, the foregoing discussion discloses and describes merely exemplary embodiments of the present invention. As will be understood by those skilled in the art, the present disclosure may be embodied in other specific forms without departing from the spirit or essential characteristics thereof. Accordingly, the present disclosure is intended to be illustrative and not limiting of the scope, as well as the claims. The disclosure, including any readily discernible variants of the teachings herein, defines in part, the scope of the foregoing claim terminology such that no subject matter is dedicated to the public.

The invention claimed is:

1. A method of performing image segmentation to detect lesions, the method comprising:

receiving by circuitry an X-ray image of a region including the lesion;

filtering the received image by a median filter to reduce speckle noise present in the received image, and forming a filtered image including a plurality of pixels;

clustering each image pixel of the plurality of pixels in the filtered image into one of a lesion region and a background region, to form a clustered image;

transforming each pixel included in the clustered image into a neutrosophic domain;

determining by the circuitry, the neutrosophic domain of each pixel by computing a three-tuple including a first probability corresponding to the pixel being correctly clustered in the lesion region, a second probability corresponding to the pixel being incorrectly clustered in the lesion region, and a third probability corresponding to the pixel being an indeterminate pixel;

iteratively computing by the circuitry, until a stop criterion is satisfied, the first probability, the second probability, and the third probability based on a mean value of pixel intensity of a predetermined window and a homogeneity value; and assigning the indeterminate pixel to one of the lesion region and the background region to segment the X-ray image upon the stopping criterion being satisfied, the assigning being performed based on a degree of pixel indeterminacy.

2. The method of claim 1, further comprising:

initializing by circuitry, a membership matrix indicating a membership value of each pixel belonging to one of the lesion region, the background region, and being the indeterminate pixel;

transforming the computed first probability, second probability, and the third probability into a first vector, a second vector, and a third vector;

computing a center vector based on the transformed vectors; and updating the membership matrix based on the computed center vector, and a number of clusters in the clustered image.

3. The method of claim 1, further comprising:

computing by circuitry, a distribution of indeterminate pixels in the lesion region and the background region, the distribution being computed based on at least an entropy that is computed in the neutrosophic domain.

4. The method of claim 1, wherein the first probability (T) of pixel (i, j) is computed as:

$$T(i, j) = \frac{\overline{g(i, j)} - \overline{g}_{min}}{\overline{g}_{max} - \overline{g}_{min}}$$

wherein, $\overline{g(i,j)}$ is a local mean value of intensity of the pixel, $\overline{g}_{min}$ is a minimum intensity value of the pixel, and $\overline{g}_{max}$ is a maximum intensity value of the pixel.

5. The method of claim 4, wherein the third probability corresponding to the pixel being indeterminate I(i, j) is computed as:

$$I(i, j) = 1 - \frac{Ho(i, j) - Ho_{min}}{Ho_{max} - Ho_{min}}$$

wherein, Ho(i, j) corresponds to a homogeneity value of the pixel, the homogeneity value being computed as a variance of pixel intensity and the local mean value of intensity of the pixel, and $Ho_{max}$ and $Ho_{min}$ correspond to a maximum and minimum value of homogeneity, respectively.

6. The method according to claim 2, wherein the center vector ($C_v$) is computed as:

$$C_v = \frac{\sum_{x=1}^{N} u_{wz}^m \cdot (1 - VI_x) \cdot VT_x \cdot VF_x}{\sum_{x=1}^{N} u_{wz}^m \cdot (1 - VI_x)}$$

wherein, $VI_x$, $VT_x$, and $VF_x$ are the transformed vectors, N is a total number of image pixels, m corresponds to a membership parameter, and $U_{wz}$ corresponds to an entry in the membership matrix, wherein w corresponds to a pixel index, and z corresponds to a cluster index.

7. An apparatus comprising:

circuitry configured to receive an X-ray image of a region including the lesion, filter the received image by a median filter to reduce speckle noise present in the received image, and forming a filtered image including a plurality of pixels, cluster each image pixel of the plurality of pixels in the filtered image into one of a lesion region and a background region, to form a clustered image, transform each pixel included in the clustered image into a neutrosophic domain;

determine the neutrosophic domain of each pixel by computing a three-tuple including a first probability corresponding to the pixel being correctly clustered in the lesion region, a second probability corresponding to the pixel being incorrectly clustered in the lesion region, and a third probability corresponding to the pixel being an indeterminate pixel, iteratively compute, until a stop criterion is satisfied, the first probability, the second probability, and the third probability based on a mean value of pixel intensity of a predetermined window and a homogeneity value, and assign the indeterminate pixel to one of the lesion region and the background region to segment the X-ray image upon the stopping criterion being satisfied, the assigning being performed based on a degree of pixel indeterminacy.

8. The apparatus of claim 7, wherein the circuitry is further configured to:

initialize a membership matrix indicating a membership value of each pixel belonging to one of the lesion region, the background region, and being the indeterminate pixel;

transform the computed first probability, second probability, and the third probability into a first vector, a second vector, and a third vector;

compute a center vector based on the transformed vectors; and update the membership matrix based on the computed center vector, and a number of clusters in the clustered image.

9. The apparatus of claim 7, wherein the circuitry is further configured to:

compute a distribution of indeterminate pixels in the lesion region and the background region, the distribution being computed based on at least an entropy that is computed in the neutrosophic domain.

10. The apparatus of claim 7, wherein the first probability (T) of pixel (i, j) is computed as:

$$T(i, j) = \frac{\overline{g(i, j)} - \overline{g}_{min}}{\overline{g}_{max} - \overline{g}_{min}}$$

wherein, $\overline{g(i,j)}$ is a local mean value of intensity of the pixel, $\overline{g}_{min}$ is a minimum intensity value of the pixel, and $\overline{g}_{max}$ is a maximum intensity value of the pixel.

11. The apparatus of claim 10, wherein the third probability corresponding to the pixel being indeterminate I(i, j) is computed as:

$$I(i, j) = 1 - \frac{Ho(i, j) - Ho_{min}}{Ho_{max} - Ho_{min}}$$

wherein, Ho(i, j) corresponds to a homogeneity value of the pixel, the homogeneity value being computed as a variance of pixel intensity and the local mean value of intensity of the pixel, and $Ho_{max}$ and $Ho_{min}$ correspond to a maximum and minimum value of homogeneity, respectively.

12. The apparatus according to claim 8, wherein the center vector ($C_v$) is computed as:

$$C_v = \frac{\sum_{x=1}^{N} u_{wz}^m \cdot (1 - VI_x) \cdot VT_x \cdot VF_x}{\sum_{x=1}^{N} u_{wz}^m \cdot (1 - VI_x)}$$

wherein, $VI_x$, $VT_x$, and $VF_x$ are the transformed vectors, N is a total number of image pixels, m corresponds to a membership parameter, and $U_{wz}$ corresponds to an entry in the membership matrix, wherein w corresponds to a pixel index, and z corresponds to a cluster index.

13. A non-transitory computer readable medium including computer executable instructions that, when executed by a computer, causes the computer to execute a method of performing image segmentation to detect lesions, the method comprising:
receiving an X-ray image of a region including the lesion;
filtering the received image by a median filter to reduce speckle noise present in the received image, and forming a filtered image including a plurality of pixels;
clustering each image pixel of the plurality of pixels in the filtered image into one of a lesion region and a background region, to form a clustered image;
transforming each pixel included in the clustered image into a neutrosophic domain;
determining the neutrosophic domain of each pixel by computing a three-tuple including a first probability corresponding to the pixel being correctly clustered in the lesion region, a second probability corresponding to the pixel being incorrectly clustered in the lesion region, and a third probability corresponding to the pixel being an indeterminate pixel;
iteratively computing, until a stop criterion is satisfied, the first probability, the second probability, and the third probability based on a mean value of pixel intensity of a predetermined window and a homogeneity value; and
assigning the indeterminate pixel to one of the lesion region and the background region to segment the X-ray image upon the stopping criterion being satisfied, the assigning being performed based on a degree of pixel indeterminacy.

14. The non-transitory computer readable medium of claim 13, further comprising:
initializing a membership matrix indicating a membership value of each pixel belonging to one of the lesion region, the background region, and being an indeterminate pixel;
transforming the computed first probability, second probability, and the third probability into a first vector, a second vector, and a third vector;
computing a center vector based on the transformed vectors; and
updating the membership matrix based on the computed center vector and a number of clusters in the clustered image.

15. The non-transitory computer readable medium of claim 13, further comprising:
computing a distribution of indeterminate pixels in the lesion region and the background region, the distribution being computed based on at least an entropy that is computed in the neutrosophic domain.

16. The non-transitory computer readable medium of claim 13, wherein the first probability (T) of pixel (i, j) is computed as:

$$T(i, j) = \frac{\overline{g(i, j)} - \overline{g}_{min}}{\overline{g}_{max} - \overline{g}_{min}}$$

wherein, $\overline{g(i,j)}$ is a local mean value of intensity of the pixel, $\overline{g}_{min}$ is a minimum intensity value of the pixel, and $\overline{g}_{max}$ is a maximum intensity value of the pixel.

17. The non-transitory computer readable medium of claim 16, wherein the third probability corresponding to the pixel being indeterminate I(i, j) is computed as:

$$I(i, j) = 1 - \frac{Ho(i, j) - Ho_{min}}{Ho_{max} - Ho_{min}}$$

wherein, Ho(i, j) corresponds to a homogeneity value of the pixel, the homogeneity value being computed as a variance of pixel intensity and the local mean value of intensity of the pixel, and $Ho_{max}$ and $Ho_{min}$ correspond to a maximum and minimum value of homogeneity, respectively.

18. The non-transitory computer readable medium of claim 17, wherein the center vector ($C_v$) is computed as:

$$C_v = \frac{\sum_{x=1}^{N} u_{wz}^m \cdot (1 - VI_x) \cdot VT_x \cdot VF_x}{\sum_{x=1}^{N} u_{wz}^m \cdot (1 - VI_x)}$$

wherein, $VI_x$, $VT_x$, and $VF_x$ are the transformed vectors, N is a total number of image pixels, m corresponds to a membership parameter, and $U_{wz}$ corresponds to an entry in the membership matrix, wherein w corresponds to a pixel index, and z corresponds to a cluster index.

* * * * *